United States Patent [19]

Lim et al.

[11] 4,118,563

[45] Oct. 3, 1978

[54] PRODUCTION OF 7-(2-AMINOMETHYLPHENYLACETAMIDO-3-(1-CARBOXYMETHYLTETRAZOL-5-YLTHIOMETHYL)-3-CEPHEM-4-CARBOXYLIC ACID

[75] Inventors: Gary M. F. Lim, Candiac; Yvon G. Perron, St-Lambert, both of Canada

[73] Assignee: Bristol-Myers Company, New York, N.Y.

[21] Appl. No.: 854,457

[22] Filed: Nov. 25, 1977

[51] Int. Cl.² ........................................... C07D 501/36
[52] U.S. Cl. ...................................... 544/26; 424/246
[58] Field of Search .................................... 544/30, 26

[56] References Cited

U.S. PATENT DOCUMENTS

| | | | |
|---|---|---|---|
| 3,382,241 | 5/1968 | Flynn | 260/243 |
| 3,657,232 | 4/1972 | Lemieux et al. | 260/243 C |
| 3,663,540 | 5/1972 | Lemieux et al. | 260/243 C |
| 3,759,905 | 9/1973 | Lemieux et al. | 260/243 C |
| 3,766,175 | 10/1973 | Lemieux et al. | 260/243 C |
| 3,813,376 | 5/1974 | Naito et al. | 260/243 C |
| 3,813,391 | 5/1974 | Naito et al. | 260/243 C |
| 3,814,755 | 6/1974 | Naito et al. | 260/243 C |
| 3,823,141 | 7/1974 | Naito et al. | 260/243 C |
| 3,840,535 | 10/1974 | Kaplan et al. | 260/243 C |
| 3,907,786 | 9/1975 | Maito et al. | 260/243 C |
| 3,910,899 | 10/1975 | Gottstein et al. | 260/243 C |
| 3,946,000 | 3/1976 | Maito et al. | 260/243 C |
| 3,966,710 | 6/1976 | McFarland et al. | 260/243 C |
| 4,045,438 | 8/1977 | Haviv et al. | 260/243 C |

FOREIGN PATENT DOCUMENTS

| | | | |
|---|---|---|---|
| 1,350,238 | 4/1974 | United Kingdom | 260/243 C |
| 1,057,029 | 2/1967 | United Kingdom | 260/239.1 |

OTHER PUBLICATIONS

Gottstein et al., Jour. of Antibiotics, pp. 1226-1229 (1976).

Leitner et al., Antimibrobial Agents and Chemotherapy, vol. 10, No. 3, pp. 426-435 (1976).

Primary Examiner—Nicholas S. Rizzo
Attorney, Agent, or Firm—Herbert W. Taylor, Jr.

[57] ABSTRACT

A new synthetic route is provided for the production of 7-(2-aminomethylphenylacetamido)-3-(1-carboxymethyltetrazol-5-ylthiomethyl)-3-cephem-4-carboxylic acid.

4 Claims, No Drawings

PRODUCTION OF 7-(2-AMINOMETHYLPHENYLACETAMIDO-3-(1-CARBOXYMETHYLTETRAZOL-5-YLTHIOMETHYL)-3-CEPHEM-4-CARBOXYLIC ACID

BACKGROUND OF THE INVENTION

1. Field of the Invention

This invention relates to the production by a novel chemical synthesis of particular members of the cephalosporin family of antibiotics characterized by having 2-aminomethylphenylacetamido as their 7-substituent.

2. Description of the Prior Art 7-(2-aminomethylphenylacetamido)-3-(1-carboxymethyltetrazol-5-ylthiomethyl)-3-cephem-4-carboxylic acid is a potent injectable cephalosporin having the generic name ceforanide; it has also been called BL-S786 in the literature. See, for example, Gottstein et al., J. Antibiotics, 29(11), 1226–1229 (1976) and Leitner et al., Antimicrobial Agents and Chemotherapy, 10(3), 426–435 (1976) and Research Disclosure, 157, 75–76 (May, 1977). The preparation and properties of this compound have been described, for example, in the application of my colleagues filed June 11, 1976 as U.S. Ser. No. 695,231. See also Belgium 832,725 (Farmdoc 18830X).

7-(p-Aminomethylphenylacetamido)cephalosporanic acid was described in U.S. Pat. No. 3,382,241. 7-(o-, m- and p-aminomethylphenylthioacetamido)cephalosporanic acids were disclosed in U.K. Pat. No. 1,350,238 (and see U.S. Pat. Nos. 3,657,232 and 3,663,540).

7-[m-(2'-Azidoethoxy)phenylacetamido]cephalosporanic acid was hydrogenated to produce 7-[m-(2'-aminoethoxy)phenylacetamido]cephalosporanic acid in U.S. Pat. No. 3,759,905 and the 3-acetoxy group was displaced by various heterocyclic thiols. Other thiolated 7-(o-aminomethylphenylacetamido)cephalosporins were disclosed in U.S. Pat. No. 3,766,175 (which contains an extensive review of the literature) and see also U.S. Pat. Nos. 3,813,376; 3,813,391; 3,814,755; 3,823,141; U.S. 3,907,786; 3,910,899; 3,946,000; and U.S. application Ser. No. 784,885 filed Apr. 5, 1977.

Recently issued U.S. Pat. No. 4,045,438 contains claim 1 reading

A compound selected from a base of the formula

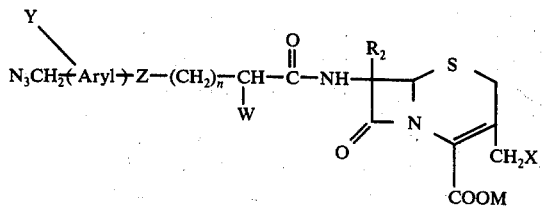

wherein Aryl is selected from phenyl and 2-thienyl; Y is selected from hydrogen, chlorine, bromine, a straight or branched lower alkyl group of from 1 to 4 carbon atoms and a lower alkoxy group of from 1 to 4 carbon atoms with the proviso that when Aryl is 2-thienyl, Y is hydrogen; Z is selected from a bond, oxygen, sulfur and imino with proviso that when Aryl is 2-thienyl, Z is a bond; W is selected from hydrogen, methyl, amino, hydroxy, $SO_3H$ and $COOR_1$ wherein $R_1$ is selected from hydrogen and 5-indanyl; n is zero, 1 or 2 with the proviso that when W is other than hydrogen or methyl and Z is other than a bond, n is not zero; $R_2$ is selected from hydrogen, and methoxy; M is selected from hydrogen; a pharmaceutically acceptable non-toxic cation; alkanoyloxymethyl wherein the alkanoyl moiety contains from 1 to 5 carbon atoms and may be straight or branched; alkanoylaminomethyl wherein the alkanoyl moiety contains from 1 to 5 carbon atoms and may be straight or branched and wherein the amino nitrogen atom may be substituted with an alkyl group of from 1 to 4 carbon atoms; alkoxycarbonylaminomethyl wherein the alkoxy moiety contains from 1 to 4 carbon atoms and may be straight or branched and wherein the amino nitrogen atom may be substituted with an alkyl group of from 1 to 4 carbon atoms; p-(alkanoyloxy)benzyl wherein the alkanoyl moiety contains from 1 to 5 carbon atoms and may be straight or branched; and aminoalkanoyloxymethyl wherein the alkanoyl moiety contains from 2 to 15 carbon atoms and the amino nitrogen may be mono- or di-substituted with a lower alkyl group of from 1 to 4 carbon atoms; X is hydrogen or acetoxy; and pharmaceutically acceptable salts thereof, and claim 26 reading A compound selected from a base of the formula:

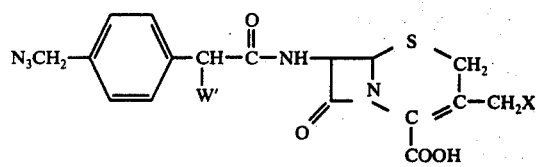

wherein W' is selected from hydrogen, hydroxy, amino, COOH and $SO_3H$; X' is hydrogen or acetoxy; and wherein the hydrogen atoms at the 6- and 7-positions are cis to one another; and pharmaceutically acceptable salts thereof, and claim 29 reading "A compound of claim 26 which is 3-[(acetyloxy)methyl[-7-[[2-[4-(azidomethyl)phenyl]-2-aminoacetyl]-amino]-8-oxo-5-thia-1-azabicyclo[4.2.0]oct-2-ene-2-carboxylic acid and pharmaceutically acceptable salts thereof", (and see Examples 15 and 19).

All of the specific disclosure of this patent is limited to azidomethyl substituents in the para position. Various 3-thiolated analogs are disclosed, e.g. for "X" in the formulae of claims 1 and 26. No aminomethyl substituents are disclosed.

U.S. Pat. No. 3,966,710 discloses compounds in the penicillin series having a ortho-aminomethylphenyl substituent such as 6-(o-aminomethylphenylacetamido)-penicillanic acid and refers to other related disclosures as in U.K. No. 1,057,029.

SUMMARY OF THE INVENTION

There is provided by the present invention, in the process for the production of the cephalosporin having the formula

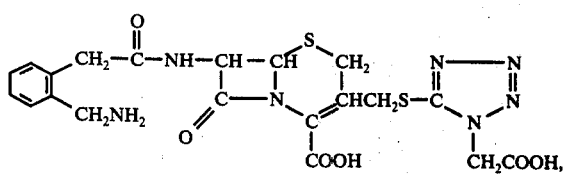

the improvement which comprises the consecutive steps of
(a) reacting 7-aminocephalosporanic acid or a salt thereof with the acid having the formula

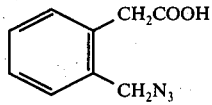

or its functional equivalent as an acylating agent for a primary amino group to produce the acid having the formula

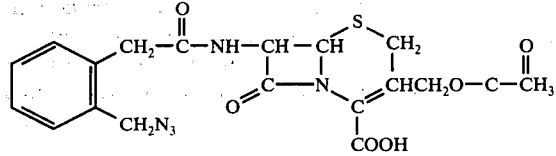

and then
(b) reacting said acid with the thiol having the formula

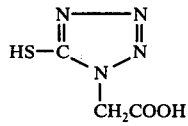

or a salt thereof to produce the compound of the formula

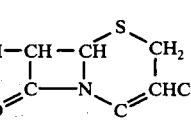

and then, preferably without isolating said compound,
(c) hydrogenating said compound in the presence of Raney nickel to produce the final cephalosporin.

There is further provided by the present invention, in the process for the production of the cephalosporin having the formula

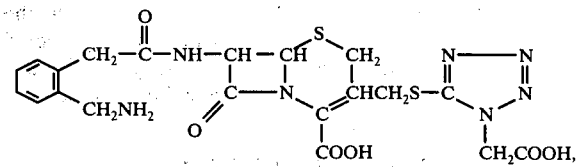

the improvement which comprises the consecutive steps of
(a) reacting the acid having the formula

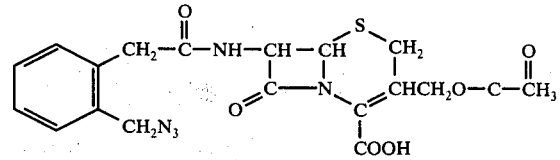

with the thiol having the formula

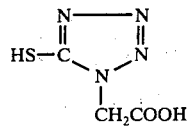

or a salt thereof to produce the compound of the formula

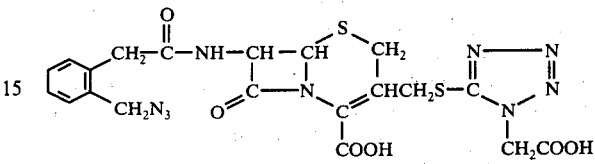

and then, preferably without isolating said compound,
(b) hydrogenating said compound in the presence of Raney nickel to produce the final cephalosporin.

There is further provided by the present invention the acid having the formula

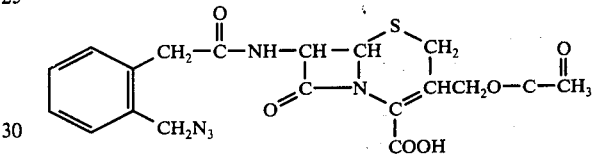

and the salts of said acid.

There is also provided by the present invention the acid having the formula

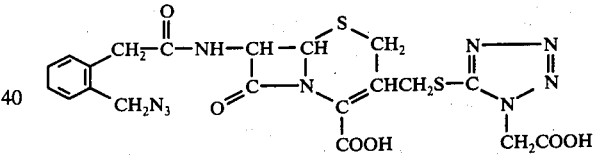

and the salts of said acid.

With respect to the said o-azidomethylphenylacetic acid used to couple with 7-aminocephalosporanic acid, functional equivalents include the corresponding acid anhydrides, including mixed anhydrides and particularly the mixed anhydrides prepared from stronger acids such as the lower aliphatic monoesters of carbonic acid, or alkyl and aryl sulfonic acids and of more hindered acids such as diphenylacetic acid. In addition, an acid azide or an active ester of thioester (e.g., with p-nitrophenyl, 2,4-dinitrophenol, thiophenol, thioacetic acid) may be used or the free acid itself may be coupled with 7-aminocephalosporanic acid after first reacting said free acid with N,N'-dimethylchloroformiminium chloride [cf. Great Britain, 1,008,170 and Novak and Weichet, Experientia XXI, 6, 360 (1965)] or by the use of enzymes or of an N,N'-carbonyldiimidazole or an N,N'-carbonylditriazole [cf. South African patent specification No. 63/2684] or a carbodiimide reagent [especially N,N'-dicyclohexylcarbodiimide, N,N'-diisopropylcarbodiimide or N-cyclohexyl-N'-(2-morpholinoethyl)carbodiimide; cf. Sheehan and Hess, J. Amer. Chem. Soc., 77, 1067 (1955)] or of alkylamine reagent [cf. R. Buijle and H. G. Viehe, Angew Chem. International Edition 3, 582 (1964)], or of a ketenimine reagent [cf. C. L. Stevens and M. E. Munk, J. Amer. Chem. Soc., 80, 4065 (1958)] or of an isoxazolium salt reagent [cf. R. B. Woodward, R. A. Olofson and H. Mayer, J. Amer. Chem. Soc., 83, 1010 (1961)]. Another equivalent of the acid chloride is a corresponding azolide, i.e., an amide of the corresponding acid whose amide nitrogen is a member of a quasiaromatic five-membered ring containing at least two nitrogen atoms, i.e., imidazole, pyrazole, the triazoles, benzimidazole, benzotriazole and their substituted derivatives. As an example of the general method for the preparation of an azolide, N,N'-carbonyldiimidazole is reacted with a carboxylic acid in equimolar proportions at room temperature in tetrahydrofuran, chloroform, dimethylformamide or a similar inert solvent to form the carboxylic acid imidazolide in practically quantitative yield with liberation of carbon dioxide and one mole of imidazole. Dicarboxylic acids yield diimidazolide. The by-product, imidazole, precipitates and may be separated and the imidazolide isolated, but this is not essential. The methods for carrying out these reactions to produce a cephalosporin and the methods used to isolate the cephalosporin so produced are well known in the art.

Nontoxic salts referred to herein are the cationic salts of the carboxylic acid group including nontoxic metallic salts such as sodium, potassium, calcium and aluminum, the ammonium salt and substituted ammonium salts, e.g. salts of such nontoxic amines as trialkylamines, including triethylamine, procaine, dibenzylamine, N-benzyl-betaphenethylamine, 1-ephenamine, N,N'-dibenzylethylenediamine, dehydroabietylamine, N,N'-bis-dehydroabietylethylenediamine, N-(lower)alkylpiperidine, e.g. N-ethylpiperidine, and other amines which have been used to form salts with benzylpenicillin.

The 7-aminocephalosporanic acid used in the coupling reaction may also be in the form of a salt or an easily hydrolyzed ester thereof including those of U.S. Pat. No. 3,284,451 and U.K. 1,229,453 and any of the silyl esters described in U.S. Pat. No. 3,249,622 for use with 6-aminopenicillanic acid or used in U.K. 1,073,530.

The reduction with hydrogen and Raney nickel is performed at conventional temperatures (preferably room temperature) and pressures in the usual solvents of which water is preferred.

DESCRIPTION OF THE PREFERRED EMBODIMENTS

REACTION SCHEME

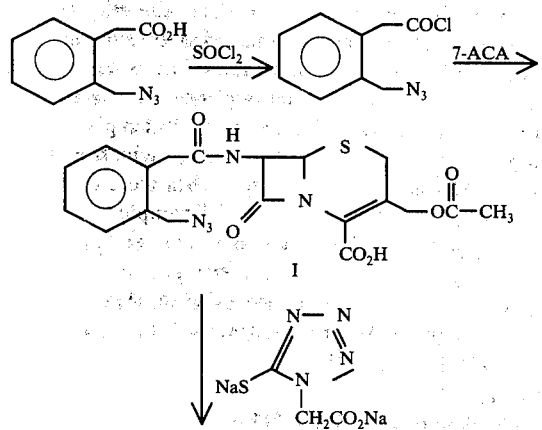

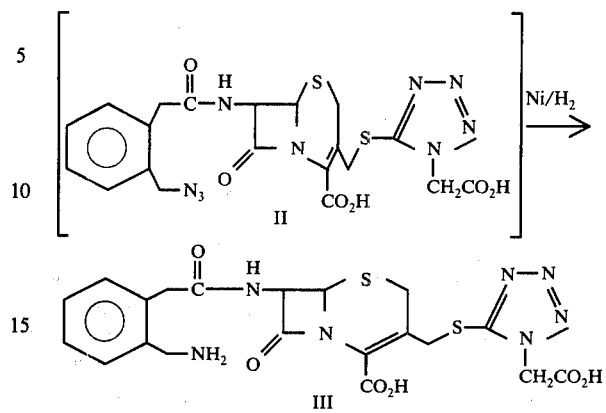

EXAMPLE 1

7-(2-Azidomethylphenylacetamido)-3-acetoxymethyl-3-cephem-4-carboxylic Acid (I)

A. Preparation of 2-Azidomethylphenylacetyl Chloride

2-Azidomethylphenylacetic acid (19.1 g., 0.1 mole) was dissolved in 800 ml. of methylene chloride. To this solution was added slowly thionyl chloride (26 g., 0.2 mole) and 0.5 ml. of dimethylformamide as catalyst. The reaction mixture was heated at reflux temperature under nitrogen atmosphere for 1 hour. The methylene chloride solution was concentrated with the aid of vacuum and the residue oil (checked by IR spectroscopy-carboxyl 1800 cm$^{-1}$ and azido group at 2010 cm$^{-1}$) was picked up in 100 ml. of acetone and placed into a dropping funnel for use directly in the subsequent acylation reaction.

B. Acylation of 7-ACA

Pulverized 7-ACA (7-aminocephalosporanic acid) (22 g., 0.08 mole) was suspended in 400 ml. of water and cooled to 5° C. N-Methylmorpholine (20 g., 0.2 mole) was added portionwise with stirring. After a solution was obtained, 300 ml. of acetone was added. The acid chloride solution from part A was added dropwise over 15 min. at 0° to 5° C. After the addition was completed the reaction mixture was stirred at 0° to 5° C. for one hour and then the acetone was distilled off with the aid of vacuum. The remaining aqueous solution was extracted with 300 ml. of toluene and to the aqueous layer was added 200 ml. of ethyl acetate; it was then cooled to 5° C. The two-layer solution was acidified with phosphoric acid (85% diluted with equal volume of water) to pH 2. The aqueous layer was separated and extracted once more with 100 ml. of ethyl acetate. The combined ethyl acetate extracts were first treated with carbon and then concentrated to a residual solid with the aid of vacuum. The residual solid was triturated with 100 ml. of toluene and then collected by filtration. After vacuum drying to constant weight (the yield was 80%), 28.5 g. of 7-(2-azidomethylphenylacetamido)-3-acetoxymethyl-3-cephem-4-carboxylic acid was obtained, m.p. 126° C. (dec.). Its NMR and IR spectroscopic data were consistent with the expected structure. The purity of the product was checked by liquid chromatography (1c).

EXAMPLE 2

7-(2-Azidomethylphenylacetamido)-3-(1-carboxymethyltetrazol-5-ylthiomethyl)-3-cephem-4-carboxylic Acid (II)

By Nucleophilic Displacement of the Acetoxy Moiety in 7-(2-Azidomethylphenylacetamido)-3-acetoxymethyl-3-cephem-4-carboxylic Acid.

7-(2-Azidomethylphenylacetamido)-3-acetoxymethyl-3-cephem-4-caboxylic acid (4.45 g., 0.01 mole) was suspended in 100 ml. of water. The pH was adjusted to 6.5 using saturated sodium bicarbonate solution. To this solution was added 1-carboxymethyl-5-mercaptotetrazole as the disodium salt (2.04 g., 0.01 mole) and the pH was adjusted to 7. The reaction mixture was heated at 70° C. for 2 hours under a nitrogen atmosphere and, after cooling, the insoluble material that remained in suspension was filtered off. The filtrate can be used directly for hydrogenation or the crude product can be isolated from it by adjusting the pH of the solution to 2.6 and then extracting twice with 30 ml. portions of ethyl acetate. The combined ethyl acetate extract was carbon treated and dried over anhydrous sodium sulfate. After filtration the ethyl acetate solution was concentrated to give an 85% yield of a 7-(2-azidomethylphenylacetamido)-3-(1-carboxymethyltetrazol-5-ylthiomethyl)-3-cephem-4-carboxylic acid as a foam-like product (estimated to be 75% pure by 1c).

EXAMPLE 3

7-(2-Aminomethylphenylacetamido)-3-(1-carboxymethyltetrazol-5-ylthiomethyl)-3-cephem-4-carboxylic Acid (III)

The aqueous filtrate from the above nucleophilic displacement with disodium salt of 1-carboxymethyl-5-mercaptotetrazole on 4.4 g. of 7-(2-azidomethylphenylacetamido)-3-acetoxymethyl-3-cephem-4-carboxylic acid in 100 ml. of water (or an aqueous solution of II that was adjusted to pH 7 with sodium bicarbonate) was placed in a hydrogenating bottle along with 4 g. of Raney nickel (washed until neutral with water) and shaken for one-half hour at room temperature and 50 psi of hydrogen (Paar hydrogenator). After the catalyst was filtered off, 50 ml. of ethyl acetate was added. The two-layer solution was cooled to 0° C. and then adjusted to pH 2.4 to 3 with 6N hydrochloric acid. The crude 7-(2-aminomethylphenylacetamido)-3-(1-carboxymethyltetrazol-5-ylthiomethyl-3-cephem-4-carboxylic acid that was suspended in the two layer solution was collected by filtration, washed once with 30 ml. of water and once with 30 ml. of ethyl acetate and was dried in vacuum to constant weight. The yield was 3.3 g. or 63.6% of theoretical (estimated by 1c to be 95% pure). A sample was purified and was found to be identical in every way to an authentic sample.

EXAMPLE 4

REACTION SCHEME

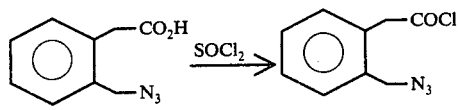

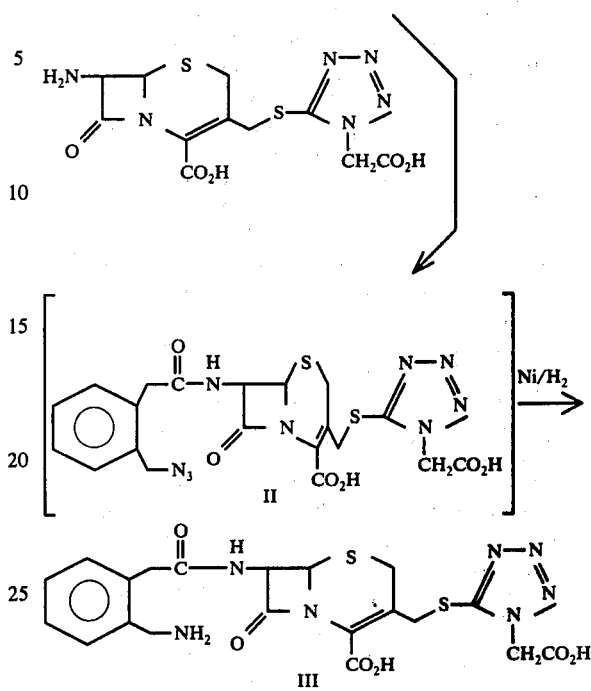

7-(2-Azidomethylphenylacetamido)-3-(1-carboxymethyltetrazol-5-ylthiomethyl)-3-cephem-4-carboxylic Acid (II)

From Acylation of 7-Amino-3-(1-carboxymethyltetrazol-5-ylthiomethyl)-3-cephem-4-carboxylic Acid.

7-Amino-3-(1-carboxymethyltetrazol-5-ylthiomethyl)-3-cephem-4-carboxylic acid (3 g., 0.008 mole) was suspended in 50 ml. of water. The suspension was cooled to 0° C. and then N-methylmorpholine (3 g., 0.03 mole) was added. After a solution was obtained, 50 ml. of acetone was added. An acetone solution of 2-azidomethylphenylacetyl chloride (prepared from 2 g. of 2-azidomethylphenyl acetic acid and 2 ml. of thionyl chloride in 100 ml. of methylene chloride) was added dropwise at 0° to 5° C. over 10 minutes. The resulting mixture was stirred for one hour and then the acetone was distilled off with the aid of vacuum. The aqueous layer was extracted once with 50 ml. of toluene. To the aqueous layer was added 50 ml. of ethyl acetate and the pH was adjusted to 2.6 using phosphoric acid (85% diluted with equal volume of water). The ethyl acetate layer was carbon treated and dried over anhydrous sodium sulfate. After filtration the solution was concentrated to give 7-(2-azidomethylphenylacetamido)-3-(1-carboxymethyltetrazol-5-ylthiomethyl)-3-cephem-4-caboxylic acid as a foam-like product which weighed 3.6 g. NMR and IR spectroscopy data were consistent with the expected structure. A small sample was hydrogenated in water using Raney nickel as catalyst to give a product which was identical in every way to an authentic sample of 7-(2-aminomethylphenylacetamido)-3-(1-carboxymethyltetrazol-5-ylthiomethyl)-3-cephem-4-carboxylic acid (III).

We claim:

1. The acid having the formula

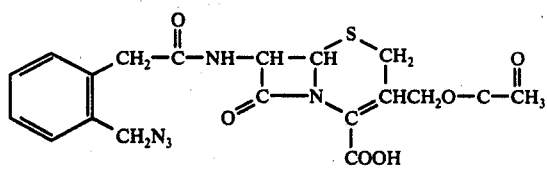

2. The acid having the formula

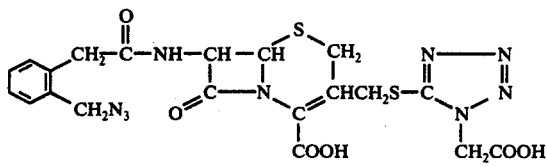

3. In the process for the production of the final cephalosporin having the formula

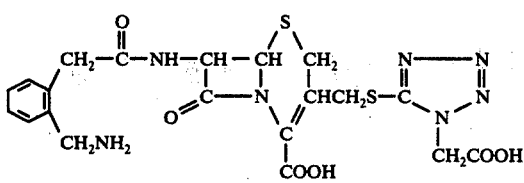

the consecutive steps of
(a) mixing 7-aminocephalosporanic acid or a salt thereof with the acid chloride having the formula

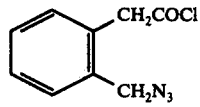

to produce the acid having the formula

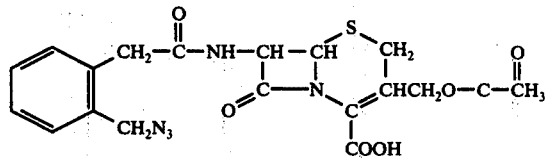

and then
(b) mixing said acid with the thiol having the formula

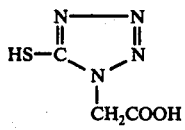

as the disodium salt thereof to produce the compound of the formula

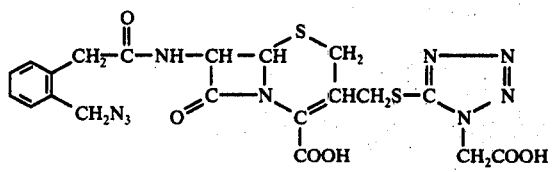

and then
(c) shaking a solution of said compound with hydrogen under pressure in the presence of Raney nickel to produce the final cephalosporin.

4. In the process for the production of the final cephalosporin having the formula

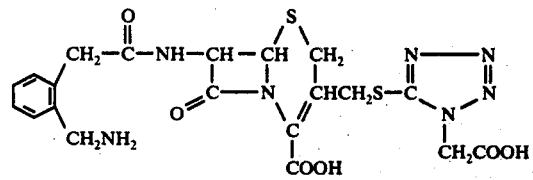

the consecutive steps of
(a) heating the acid having the formula

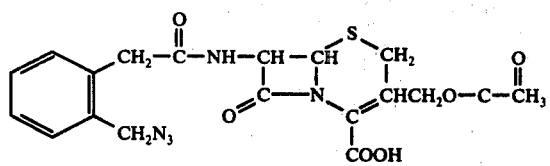

with the thiol having the formula

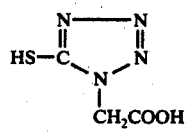

as the disodium salt thereof in water at about pH 7 to produce the compound of the formula

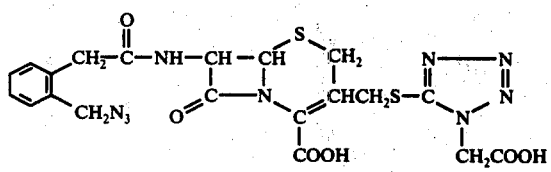

in solution, filtering said solution to provide a filtrate containing said compound and then
(b) shaking said filtrate with hydrogen under pressure in the presence of Raney nickel to produce the final cephalosporin.

* * * * *